(12) United States Patent
Stockel et al.

(10) Patent No.: US 9,023,891 B2
(45) Date of Patent: *May 5, 2015

(54) SYNERGISTIC ANTIMICROBIAL AGENTS

(75) Inventors: Richard F. Stockel, Bridgewater, NJ (US); Anthony J. Sawyer, Albuquerque, NM (US)

(73) Assignee: Nevada Naturals, Inc., Albuquerque, NM (US)

(*) Notice: Subject to any disclaimer, the term of this patent is extended or adjusted under 35 U.S.C. 154(b) by 333 days.

This patent is subject to a terminal disclaimer.

(21) Appl. No.: 13/465,489

(22) Filed: May 7, 2012

(65) Prior Publication Data

US 2012/0225942 A1    Sep. 6, 2012

Related U.S. Application Data

(63) Continuation-in-part of application No. 12/455,197, filed on May 28, 2009, now Pat. No. 8,193,244.

(60) Provisional application No. 61/130,225, filed on May 29, 2008.

(51) Int. Cl.
| | |
|---|---|
| *A61K 31/215* | (2006.01) |
| *A61K 31/24* | (2006.01) |
| *A01N 25/00* | (2006.01) |
| *A61K 8/49* | (2006.01) |
| *A01N 37/02* | (2006.01) |
| *A61K 8/37* | (2006.01) |
| *A61K 8/44* | (2006.01) |
| *A61Q 19/00* | (2006.01) |

(52) U.S. Cl.
CPC ............... *A61K 8/492* (2013.01); *A01N 37/02* (2013.01); *A61K 8/375* (2013.01); *A61K 8/44* (2013.01); *A61K 8/4946* (2013.01); *A61Q 19/00* (2013.01); *A61K 2800/10* (2013.01); *A61K 2800/524* (2013.01)

(58) Field of Classification Search
CPC .... A01N 37/20; A01N 3/16; A01N 2300/007
USPC .................................. 514/529, 534; 424/405
See application file for complete search history.

(56) References Cited

U.S. PATENT DOCUMENTS

| | | | |
|---|---|---|---|
| 3,825,560 A | 7/1974 | Saito et al. | |
| 4,299,852 A * | 11/1981 | Ueno et al. ................... | 426/266 |
| 4,997,851 A | 3/1991 | Isaacs et al. | |
| 5,434,182 A | 7/1995 | Isaacs et al. | |
| 5,780,658 A | 7/1998 | Martinez-Pardo et al. | |
| 6,414,023 B1 | 7/2002 | Brandsborg et al. | |
| 6,638,978 B1 | 10/2003 | Kabara | |
| 7,074,447 B2 | 7/2006 | Bonaventura et al. | |
| 7,087,769 B1 | 8/2006 | Contijoch Mestres | |
| 2004/0122095 A1 | 6/2004 | Bonaventura et al. | |
| 2004/0166082 A1 | 8/2004 | Urgell-Beltran et al. | |
| 2004/0175350 A1 | 9/2004 | Urgell-Beltran et al. | |
| 2004/0254232 A1 | 12/2004 | Urgell-Beltran et al. | |
| 2004/0265443 A1 | 12/2004 | Urgell-Beltran et al. | |
| 2005/0084471 A1 | 4/2005 | Andrews | |
| 2005/0175747 A1 | 8/2005 | Seguer Bonaventura et al. | |
| 2005/0181041 A1 | 8/2005 | Goldman | |
| 2006/0030512 A1 | 2/2006 | Hart | |
| 2010/0056628 A1 | 3/2010 | Stockel | |
| 2010/0173993 A1 | 7/2010 | Sawyer | |
| 2011/0177140 A1 | 7/2011 | Voegeli et al. | |

FOREIGN PATENT DOCUMENTS

| | | |
|---|---|---|
| WO | WO0197851 A2 | 12/2001 |
| WO | WO 2007/014580 A1 * | 2/2007 |
| WO | WO2008/014824 | 2/2008 |

OTHER PUBLICATIONS

International Search Report of the International Searching Authority mailed on Mar. 25, 2013 in the corresponding international application No. PCT/US2012/036869.

* cited by examiner

*Primary Examiner* — Shengjun Wang
(74) *Attorney, Agent, or Firm* — Posz Law Group, PLC

(57) ABSTRACT

Synergistic antimicrobial compositions are provided by combining effective amounts of $N^\alpha$-long chain alkanoyl di basic amino acid alkyl ester salts with glycerol monofatty acid esters resulting more effective anti-microbials and food preservatives.

19 Claims, No Drawings

SYNERGISTIC ANTIMICROBIAL AGENTS

CROSS-REFERENCE TO RELATED APPLICATIONS

This application is a continuation-in-part of application U.S. Ser. No. 12/455,197 filed May 28, 2009, which claims the benefit of provisional application U.S. Ser. No. 61/130,225 filed May 29, 2008.

BACKGROUND OF THE INVENTION

One important factor in choosing ingredients for foods and cosmetics is the requirement to select only those that are human safe and environmentally benign. The use of GRAS and especially natural or naturally-derived materials, i.e. those referred to as "green", is also very much of interest in topically applied and ingested compositions. Thus, such materials reduce the likelihood of adverse reactions to the human body if absorbed into the body through the skin.

Although food safe and naturally derived $N^\alpha$-long chain alkanoyl di basic amino acid alkyl ester salts have been known since the 1960's, one of the first patents to recommend these amino acids, specifically for food applications was U.S. Pat. No. 3,825,560 (issued Jul. 23, 1979). A number of derivatives are disclosed including $N^\alpha$-cocoyl-L-arginine ethyl ester pyrrolidone carboxylate and $N^\alpha$-lauroyl-L-arginine methyl ester hydrochloride. Since this publication, there have been several more patents issued or published disclosing specifically $N^\alpha$-lauroyl-L-arginine ethyl ester hydrochloride salt (LAE-HCl). These include U.S. Pat. No. 5,780,658 that discloses a process to prepare LAE-HCl, as well as disclosing its use for food applications. U.S. Pat. No. 7,074,447 B2 discloses an antimicrobial composition comprising LAE-HCl with potassium sorbate. U.S. Pat. No. 7,087,769 is another process patent suggesting its use for food. Two patent publications, U.S. 2004/0166082 and U.S. 2004/0175350, disclose dibasic amino acid alkyl ester salts useful for cosmetic applications. U.S. 2004/0254232 covers the oral care use while U.S. 2004/0265443 covers food. U.S. 2005/0175747 discloses complexes formed between LAE-HCl and various anionic hydrocolloids.

In addition to bacteria, fungi, yeasts and molds, many cationic surfactants are known for their anti-viral activity. Indeed, US patent publication U.S. 2009/0326031 discloses the use of $N^\alpha$-lauroyl-L-arginine ethyl ester hydrochloride for the prevention and treatment of viral infections including influenza and herpes viruses.

The literature provides numerous references concerning glycerol monofatty acid esters having antiviral and antibacterial activity. The most active monoglycerides consist of those esters formed from saturated fatty acids having from 6 to 14 carbon atoms. U.S. Pat. No. 4,997,851 teaches the use of saturated fatty acids and glycerol monofatty acid esters as effective antiviral agents against the HIV and HSV-1 viruses. They were also active against a variety of gram positive and gram-negative bacteria.

U.S. Pat. No. 5,434,182 discloses the spermicidal, antimicrobial and cytocidal activity of glycerol monofatty acid esters. It discloses the combination of fatty acyl glycerides, a chelating acid, and a surfactant which confer excellent antimicrobial activity for preserving processed meats and for disinfecting poultry carcasses. When only one of these three agents was used, the anti-microbial performance was considerably reduced. U.S. Pat. No. 6,414,023 B1 discloses the use of fatty acid monoglycerides in conjunction with 2,4-dichlorobenzyl alcohol.

U.S. Pat. No. 6,638,978 B1 lists a preservative formulation for food and cosmetics consisting of glyceryl mono-laurate (monolaurin, ML), a mixture of caprylic and capric acid and propylene glycol in an aqueous base. U.S. 2005/0084471 A1 teaches the preparation of a preservative for meat, fruits, and vegetables and for the disinfection of inanimate surfaces. The actives include a propylene glycol $C_7$-$C_{14}$ fatty acid ester as the major component, a surfactant, and an enhancer. Enhancers include phenolic antioxidants and/or a paraben ester. Lastly, U.S. Patent 2006/0030512 A1 describes a long lasting anti-microbial film comprising a glycerol monoester, an amphoteric surfactant, a chelating agent and a solvent like propyl alcohol plus other incipients.

SUMMARY OF THE INVENTION

One object of this invention is the provision of a synergistic combination of $N^\alpha$-($C_8$ to $C_{16}$) alkanoyl dibasic amino acid ($C_1$ to $C_4$) alkyl ester salts and ($C_8$-$C_{14}$) fatty acid glycerol esters as the basis for antimicrobial compositions and preservatives.

A second object of the invention is the use of a synergistic combination of $N^\alpha$—$C_8$ to $C_{16}$) alkanoyl dibasic amino acid ($C_1$ to $C_4$) alkyl ester salts together with ($C_8$-$C_{14}$) fatty acid glycerol esters to control bacteria, fungi, molds, yeasts, mildews and viruses.

A third object of the invention is the use of a synergistic combination of $N^\alpha$-($C_8$ to $C_{16}$) alkanoyl dibasic amino acid ($C_1$ to $C_4$) alkyl ester salts together with ($C_8$-$C_{14}$) fatty acid glycerol esters as a preservative in foods, cosmetics and other compositions.

The synergistic compositions described above allow the use of much lower levels of either compound while maintaining effective preservative and anti-microbial activity and thereby reduce cost.

The foregoing objects and other objects of the invention will be apparent from the details of the invention set forth below.

DETAILED DESCRIPTION OF THE INVENTION

This invention provides for an antimicrobial composition comprising 1) an effective amount of an $N^\alpha$-alkanoyl-dibasic amino acid alkyl ester salt having 8 to 16 carbons in the alkanoyl chain and 1 to 4 carbon atoms in the alkyl chain, and 2) an effective amount of one or more $C_8$-$C_{14}$ saturated fatty acid monoglycerides, combined at a synergistically effective ratio.

This invention also provides for a method of killing bacteria, fungi, molds, yeasts and viruses or inhibiting their growth by the application of a composition comprising 1) an effective amount of an $N^\alpha$-alkanoyl-dibasic amino acid alkyl ester salt having 8 to 16 carbons in the alkanoyl chain and 1 to 4 carbon atoms in the alkyl chain, and 2) an effective amount of one or more C8-C14 saturated fatty acid monoglycerides, combined at a synergistically effective ratio.

This invention also provides for a method of preserving foods and cosmetic or other formulations by the application of a composition comprising 1) an effective amount of an $N^\alpha$-alkanoyl-dibasic amino acid alkyl ester salt having 8 to 16 carbons in the alkanoyl chain and 1 to 4 carbon atoms in the alkyl chain, and 2) an effective amount of one or more C8-C14 saturated fatty acid monoglycerides, combined at a synergistically effective ratio.

The $N^\alpha$-alkanoyl dibasic amino acid alkyl ester salts of specific interest for use in the above composition for controlling bacteria, fungi, molds, yeasts and viruses and for preserving foods, cosmetics and other formulations are the $N^\alpha$-long chain alkanoyl dibasic amino acid alkyl esters of L-arginine, L-histidine, L-tryptophan, ornithine and L-lysine.

The preferred dibasic amino acids for preparing the $N^\alpha$-alkanoyl-dibasic amino acid alkyl ester cation portion of the salts is L-arginine. The most preferred $N^\alpha$-alkanoyl-dibasic amino acid alkyl ester cations for use in this invention are $N^\alpha$-lauroyl-L-arginine ethyl ester cation (LAE) and $N^\alpha$-cocoyl-L-arginine ethyl ester cation (CAE).

As will be discussed below, since it is only the cationic component of the $N^\alpha$-alkanoyl-dibasic amino acid alkyl ester salt which is responsible for this compound's antimicrobial and preservative activity, the choice of the anionic component of the salt is not very important, as long as the solubility of the salt is sufficient to enable it to release a sufficient amount of the $N^\alpha$-alkanoyl-dibasic amino acid alkyl ester cation to control microbial growth when dissolved in water at RT.

It may be noted that in addition to the outstanding antimicrobial properties of soluble $N^\alpha$-long chain alkanoyl di basic amino acid alkyl ester salts, these salts are especially safe for humans and the environment. They are GRAS and hence considered completely food safe. In addition, they are naturally derived and rapidly break down into their benign natural component parts in the human body or when released in the environment. Ultimately the natural components completely metabolize in the body and fully biodegrade in the environment to simple non-toxic compounds like water, carbon dioxide and ammonium salts.

The second component of the synergistic system of this invention is a glyceryl monoalkanoate ester (acyl monoglyceride or glycerol fatty acid ester) having from 8 to 14 carbon atoms. Glyceryl monoalkanoates have a long history of safety and a low toxicity profile. Some of these esters are found naturally, for example glyceryl mono-laurate is found in human milk. The most preferred glyceryl mono-alkanoate ester for use in this composition is glyceryl monolaurate.

The synergistic combination of $N^\alpha$-long chain alkanoyl di basic amino acid alkyl ester salts together with acyl glycerides provide several advantages over using either $N^\alpha$-long chain alkanoyl dibasic amino acid alkyl ester salts or acyl monoglycerides alone. First of all, lower quantities of the combined agents are required to kill or inhibit the growth of microbes, thereby reducing costs. Secondly the combination has a broader spectrum of activity against the various microbial species including bacteria, fungi, molds, yeasts and viruses, than either compound used alone. Furthermore, one concern with preservatives is the potential loss of activity due, for example, to chemical decomposition, adsorption onto the materials being preserved or break down of the preservative due to bacterial action. One advantage of using a combination of actives, results from the possibility of one of the preservatives retaining sufficient activity if another preservative is lost. An additional advantage of the combination is a lengthening of the time that a solution provides antimicrobial activity. Another advantage of this combination is that both components are naturally derived and hence less likely to be harmful when ingested.

To demonstrate the synergistic effect of combining $N^\alpha$-long chain alkanoyl dibasic amino acid alkyl ester salts together with acyl glycerides, the MICs of various mixtures of $N^\alpha$-lauroyl arginine ethyl ester acetate salt and glyceryl monolaurate in preventing the growth of *listeria monocytogenes* were determined. The MICs (minimum inhibitory concentration) of similar mixtures of lactate salt of $N^\alpha$-lauroyl arginine ethyl ester lactate salt with glyceryl monolaurate were also measured. The results of these determinations are summarized in Table 1A and Table 1B. All percentages are in weight.

TABLE 1A

*Listeria monocytogenes*
Minimum concentration where no bacterial growth was observed.

| | LAE acetate combinations with glyceryl mono-laurate LAE acetate % | | | | |
|---|---|---|---|---|---|
| | 100 | 75 | 50 | 25 | 0 |
| ML % | 0 | 25 | 50 | 75 | 100 |
| MIC Total | 15 | 15 | 15 | 25 | 30 |
| Additive line* | 15 | 18.75 | 22.5 | 26.25 | 30 |
| MIC LAE acetate | 15 | 11.25 | 7.5 | 6.25 | 0 |
| MIC ML | 0 | 3.75 | 7.5 | 18.75 | 30 |

*The additive line indicates the calculated amount of preservative which would be considered additive and not synergistic

TABLE 1B

*Listeria monocytogenes*
Minimum concentration where no bacterial growth was observed.

| | LAE lactate combinations with glyceryl mono-laurate LAE lactate % | | | | |
|---|---|---|---|---|---|
| | 100 | 75 | 50 | 25 | 0 |
| ML % | 0 | 25 | 50 | 75 | 100 |
| MIC Total | 10 | 10 | 15 | 20 | 30 |
| Additive Effect* | 10 | 15 | 20 | 25 | 30 |
| MIC LAE lactate | 10 | 7.5 | 7.5 | 5 | 0 |
| MIC ML | 0 | 2.5 | 7.5 | 15 | 30 |

*The additive line indicates the calculated amount of preservative which would be considered additive and not synergistic The MIC results against *listeria monocytogenes* are shown in the first row of each table. The second row provides calculated values for an additive effect between the two agents. It can be seen that for both the acetate and lactate salts, the MICs determined by experimentation are lower than the numbers calculated for an additive effect, an indication of performance synergy between the $N^\alpha$-lauroyl arginine ethyl ester salt and glyceryl monolaurate (Monolaurin). Based on the results it seems reasonable to project that the synergistic antibacterial performance region extends within ratios of about 9:1 to about 1:9 of $N^\alpha$-lauroyl arginine ethyl ester salt to glyceryl monolaurate.

The third row in each Table shows the amount of $N^\alpha$-lauroyl arginine ethyl ester salt which was present in each mixture at the concentration where no bacterial growth was seen. It can be seen that the amount of ester salt, which was needed in the presence of glyceryl monolaurate was reduced with increasing concentrations of glyceryl monolaurate shown in the fourth row. Since the $N^\alpha$-lauroyl arginine ethyl ester salts are significantly more expensive than glyceryl monolaurate, it can be seen that the synergy has a significant economic benefit.

In previous studies we demonstrated that the combinations of the hydrochloride salt of $N^\alpha$-lauroyl arginine ethyl ester salt provides synergistic inhibition of growth of *candida albicans* when combined with glycerol mono-laurate. Table 2A, below, summarizes our previous findings against *Candida* yeasts.

TABLE 2A

*Candida albicans*
Minimum concentration where no *Candida* growth was observed.

LAE hydrochloride combinations
with glyceryl mono-laurate

| | LAE HCl % | | | | | | | | |
|---|---|---|---|---|---|---|---|---|---|
| | 100 | 90 | 80 | 70 | 60 | 50 | 40 | 30 | 0 |
| ML % | 0 | 10 | 20 | 30 | 40 | 50 | 60 | 70 | 100 |
| MIC Total | 30 | 20 | 15 | 15 | 10 | 15 | 15 | 15 | 20 |
| Additive line* | 30 | 29 | 28 | 27 | 26 | 25 | 24 | 23 | 20 |
| MIC LAE HCl | 30 | 18 | 12 | 10.5 | 6 | 7.5 | 6 | 4.5 | 0 |
| MIC ML | 0 | 2 | 3 | 4.5 | 4 | 7.5 | 9 | 10.5 | 20 |

*The additive line indicates the calculated amount of preservative which would be considered additive and not synergistic Based on the results it can be seen that there is a synergistic inhibition of growth of *Candida* yeasts due to combinations of $N^\alpha$-lauroyl arginine ethyl ester hydrochloride and glyceryl monolaurate. The above study was repeated in duplicate with the results shown in Table 2B.

TABLE 2B

*Candida albicans*
Average minimum concentration where no *Candida* growth was observed.

LAE hydrochloride combinations
with glyceryl mono-laurate

| | LAE HCl % | | | | | | | | | | |
|---|---|---|---|---|---|---|---|---|---|---|---|
| | 100 | 90 | 80 | 70 | 60 | 50 | 40 | 30 | 20 | 10 | 0 |
| ML % | 0 | 10 | 20 | 30 | 40 | 50 | 60 | 70 | 80 | 90 | 100 |
| MIC Total | 30 | 25 | 25 | 25 | 25 | 25 | 27.5 | 27.5 | 40 | 45 | 120 |
| Additive line* | 30 | 39 | 48 | 57 | 66 | 75 | 84 | 93 | 102 | 111 | 120 |
| MIC LAE HCl | 30 | 22.5 | 20 | 17.5 | 15 | 12.5 | 11 | 8.2 | 8 | 4.5 | 0 |
| MIC ML | 0 | 2.25 | 5 | 7.5 | 10 | 12.5 | 16.5 | 19.25 | 32 | 40.5 | 120 |

*The additive line indicates the calculated amount of preservative which would be considered additive and not synergistic While the absolute MIC results of the second study (Table 2B) were not identical to those of the first study (Table 2A), both sets of results confirm a strong synergy between the $N^\alpha$-lauroyl arginine ethyl ester acetate salt and glycerol mono-laurate in inhibiting the growth of *Candida* yeasts. Most importantly, the results indicate that the minimum amount of $N^\alpha$-lauroyl arginine ethyl ester acetate needed to inhibit *Candida* growth decreases synergistically with increasing concentrations of glyceryl monolaurate between the ratios of 9:1 to 1:9 respectively.

Based on the results, it can reasonably be projected that soluble $N^\alpha$-long chain alkanoyl dibasic amino acid alkyl ester salts will provide synergistic anti-microbial activity when combined with a glycerol mono-fatty acid ester. It would seem that in order to obtain the practical benefits of the synergism between an $N^\alpha$-long chain alkanoyl dibasic amino acid alkyl ester salt and a glycerol mono-fatty acid ester, the solubility of the $N^\alpha$-long chain alkanoyl dibasic amino acid alkyl ester salt would need to be sufficient to release a concentration of $N^\alpha$-long chain alkanoyl dibasic amino acid alkyl ester cation which is greater than microbial inhibitory concentration of that ion in water at RT. Based on the data, it would seem that the absolute minimum solubility required would be approximately 5 ppm in water at RT. Desirably, however, the solubility of the $N^\alpha$-long chain alkanoyl dibasic amino acid alkyl ester salt should be such that the amount of cation released at saturation should be significantly higher than the minimum 5 ppm to allow for flexibility in formulation, faster kill and more effective inhibition. Accordingly it would seem desirable for the $N^\alpha$-long chain alkanoyl dibasic amino acid alkyl ester salt to have a solubility greater than about 50 ppm and preferably greater than 100 ppm in water at RT. With more resistant microbial species, more soluble salts might be needed. To meet the solubility requirement, suitable anions include but are not limited to halides, glycerophosphate, gluconate, mono-carboxylates, hydroxyl-mono-carboxylates, dihydrogen phosphate, and phenolate. Preferred examples of the monocarboxylates and monohydroxycarboxylates are those with up to about 12 carbon atoms. The most preferred examples include acetate and lactate.

The total concentration of $N^\alpha$-long chain alkanoyl di basic amino acid alkyl ester salts plus glycerol mono fatty acid ester to be employed in compositions of this invention should be greater than about 15 ppm and up to about 20,000 ppm. Preferably the concentration of the combination should be between about 60 ppm and 10,000 ppm, most preferably it should be between about 300 ppm and 5,000. It should be noted that resistant organisms such as some viruses, yeasts, fungi, and molds, might even require the use of higher levels for eradication, possibly up to 2.0 wt % of the synergistic combination. To function as a preservative, the usage level of the two synergistic ingredients should generally be in the range of 100 ppm to 5000 ppm, depending on what other ingredients are present in the mixture being preserved.

Synergy between the $N^\alpha$-long chain alkanoyl dibasic amino acid alkyl ester salt and glycerol mono-fatty acid ester is achieved when the weight ratio of $N^\alpha$-long chain alkanoyl di-basic amino acid alkyl ester salt to glycerol mono-fatty acid ester is between 9:1 to 1:9. More preferably the optimum ratio of the synergistic ingredients should be between about 8.5:1.5 and about 1:4.

Synergistic combinations of $N^\alpha$-long chain alkanoyl dibasic amino acid alkyl ester salts and glyceryl monoalkanoate esters are generally effective in the pH range of between about 2.0 and 10.0. However, at pHs below about 4.0 and above about 9.0, the ester grouping on $N^\alpha$-long chain alkanoyl dibasic amino acid alkyl ester cations can hydrolyze in aqueous solution forming the inactive $N^\alpha$-long chain alkanoyl dibasic amino acid. Hence, the $N^\alpha$-long chain alkanoyl dibasic amino acid alkyl ester cationic portion of the combination should be stored at pHs preferably between about 3.5 and 7.5. However, when used where the antimicrobial system is needed over a relatively short period of time e.g. when concentrations of the antimicrobials are sufficient to reduce antimicrobial viability to the desired degree within, say 2 hours, solution pHs outside this range may be employed.

Applications

The synergistic compositions of this invention are suitable for a wide range of applications. It should be understood that this list is presented for illustrative purposes only and does not represent any limitation as to possible applications. It should be further understood that it is within the purview of this invention that, depending on the application, the synergistic combinations of the invention can be formulated or used with any other compatible ingredients to provide effective compositions for the desired use. Without being limited, examples of additional types of ingredients, which can added to synergistic combinations of the invention to produce useful compositions, include anti-microbial agents, antifungal agents, hormones, vitamins, antioxidants, hydroxy acids, silicones, humectants, emollients, synthetic or natural oils, deodorizers, perfumes, colorants, preservatives, plant extracts, surfactants, solvents, organic thickeners, inorganic thickeners, inorganic salts, chelating agents, oxidizing agents, colorants, dental abrasives, flavors, fragrance oils, etc.

Regarding surfactants, it should be noted that $N^\alpha$-long chain alkanoyl di basic amino acid alkyl ester salts are most compatible with amphoteric, nonionic and cationic. However, many anionic surfactants react with $N^\alpha$-long chain alkanoyl di basic amino acid alkyl ester salts to form insoluble and therefore inactive salts.

Non-limiting examples of applications for the synergistic combinations of the invention include antimicrobial products, household products and cleaners, fabric detergents, dish detergents, cleansers, soaps, bubble baths, disinfectants, deodorizers, foods, food products, beverages, preservative compositions, antimicrobial packaging, pharmaceutical products, medical devices, contact lenses, cosmetics, hygiene compositions, infant care products, antimicrobial soaps, hand sanitizers, deodorants, antiperspirants, anti-microbial coatings, dental compositions, toothpastes, mouthwashes, lipsticks, dental appliances, medications, athlete's foot treatments, medicated chewing gums, wound care compositions, dermatological compositions, acne treatments, skin conditioners, skin moisturizers, anti-wrinkle formulations, skin whiteners, sunscreens, tanning lotions, hair products, shampoos, shower gels, bubble baths, conditioners, shaving creams, spermicides etc. Also included are microbial-resistant fabrics and apparel, anti-microbial condoms, surgical gowns, microbial-resistant hospital equipment, anti-microbial paper products, animal care products, antimicrobial plastics, antimicrobial plastic devices, rubbers and other fabrication materials, appliances with antimicrobial constituents or coatings, etc.

With respect to food products, the synergistic compositions of this invention are particularly useful as food preservatives. They are typically incorporated into the food products being preserved or applied to the food products in the form of aqueous solutions, emulsions or microemulsions such that the composition should be present in an amount of between about 10 ppm and about 20,000 ppm of the food product, more preferably 50 to 5000 ppm of food product. The salt may be applied to the food product by any techniques for example by spraying, immersion, dipping, injection or direct addition to the food product.

Examples of foods which can be preserved with compositions of the invention include but are not limited to meats, poultry products, fish, crustaceans, vegetables, greens, emulsions, sauces, confectionery, candies, chewing gum, bakery, dairy products, egg-based products, jams, jellies, beverages, juices, wines and beers etc.

Additionally, compositions of the invention can also be added to the food packaging from where it can release preservatives into the food product being preserved. Generally where added to food packaging, the amounts of composition needed to effect food preservation would be higher than the amount needed when incorporated directly into food. Typically, from about 100 ppm to about 5% by weight of the food packaging food products would be used.

Additionally, plastics and miscellaneous products can be coated and/or impregnated with the compositions of the invention, including: medical items, e.g., thermometers, catheters, surgical sutures, blood lines, implants, bandages, surgical dressings, surgical apparel, respirators, etc.; fluid-dispensing tubing; drug and cosmetic packaging; eating utensils; shower curtains; bath mats; sponges; mops; toilet seats, rubber gloves; contact lenses; hearing aids; shelving paper; carpet pads; pool covers; animal bedding and cat litter; computer covers and computer keys; doorknobs; tampons and sanitary napkins; adult novelties; sexual aids; sex toys; pregnancy barriers; dental chairs; dryer sheets; dishcloths; paints and coatings; deodorizing liquids, solids, sprays, gels and powders; filters; foams; hair brushes; combs; diaper rash preventer; plasma bag treatment; disposable glove treatment; additive to pasteurized cow milk; additive to blood sample tubes to inactivate HIV, HCMV, and other viruses (safety measure for lab technicians and healthcare providers); additives for condoms, band-aids, or bandages; additive for paint; or animal or plant treatment for microbial infections; and the like.

Additionally, fibers and fabrics can be coated and/or impregnated with the compositions of the invention, including natural and synthetic fibers and fabrics manufactured from such fibers; wipes, cloths; surgical gauze; crib covers; bassinet covers; bed linens; towels and wash cloths; tents; draw sheets; cubicle curtains; shower curtains; wall coverings; wood and wood products; hospital clothing such as examination robes, physicians' coats, nurses uniforms, etc.; apparel; paper, non-woven fabric, knitted fabric, woven fabric, brick, stone, plastic, polymer, latex, metal, tile, walls, floors, gurneys, tables, or trays; shoes and the like.

Cleaning products can usefully incorporate synergistic combinations of the invention for the purposes of sanitizing or deodorizing surfaces. Typically, the synergistic compositions would be added to aqueous cleaning formulations in concentrations between about 100 to about 2000 ppm. Other cleaning agents can be added at the concentrations needed to make the products effective which will depend on usage concentration. Most cleaning formulations contain surfactants. As mentioned previously, virtually all nonionic, amphoteric and cationic surfactants are generally compatible with the synergistic combinations of the invention. However, most anionic surfactants will cause the $N^\alpha$-long chain alkanoyl dibasic amino acid alkyl ester salts to precipitate from solution.

The invention claimed is:

1. A composition comprising 1) an effective amount of an $N^\alpha$-alkanoyl-dibasic amino acid alkyl ester salt having 8 to 16 carbons in the alkanoyl chain and 1 to 4 carbon atoms in the alkyl chain, and 2) an effective amount of one or more saturated $C_8$-$C_{14}$ fatty acid monoglycerides, combined so that the minimum effective amount of the $N^\alpha$-alkanoyl-dibasic amino acid alkyl ester decreases synergistically with increasing concentration of the saturated C8-C14 fatty acid monoglycerides between the ratios of 9:1 to 1:9 wherein the total amount of antimicrobial, as a % by weight, is unchanged.

2. A composition of claim 1 in which the $N^\alpha$-alkanoyl-dibasic-amino acid alkyl ester salts are selected from $N^\alpha$-long chain alkanoyl-dibasic-amino acid alkyl esters of L-arginine, L-histidine, L-tryptophan, L-ornithine and L-lysine.

3. A composition of claim 2 in which the $N^\alpha$-alkanoyl-dibasic amino acid alkyl ester salt is selected from the group consisting of $N^\alpha$-Iauroyl-L-arginine ethyl ester salt and $N^\alpha$-cocoyl-L-arginine ethyl ester salt and the fatty acid monoglyceride is glyceryl mono-laurate.

4. A composition of claim 1 in which the anionic component of the $N^\alpha$ alkanoyl-dibasic amino acid alkyl ester salt is such that the solubility of the $N^\alpha$-alkanoyl-dibasic amino acid alkyl ester salt is greater than 50 ppm in water at RT.

5. A composition of claim 4 in which the anionic component of the $N^\alpha$-alkanoyl-dibasic amino acid alkyl ester salt is selected from the group consisting of a halide, glycerophosphate, gluconate, mono-carboxylate, hydroxy-mono-carboxylates, dihydrogen phosphate, and phenolate.

6. A composition of claim 5 in which the anionic monocarboxylate has a chain length of up to about 12 carbon atoms.

7. A composition of claim 5 in which the anionic hydroxy-monocarboxylate has a chain length of up to about 12 carbon atoms.

8. A composition of claim 6 in which the monocarboxylate is acetate.

9. A composition of claim 6 in which the hydroxyl monocarboxylate is lactate.

10. The composition of claim 1 in which the ratio of $N^\alpha$ alkanoyl-dibasic amino acid alkyl ester salt to fatty acid monoglyceride is in the synergistically effective antimicrobial ratio of between 8.5:1.5 and 1:4.

11. The composition of claim 1 which has a pH between about 3.5 and 7.5.

12. A method of killing bacteria, fungi, molds, yeasts and viruses or inhibiting their growth by the application of at least about 15 ppm of an antimicrobial composition comprising 1) an effective amount of an $N^\alpha$-alkanoyl-dibasic amino acid alkyl ester salt having 8 to 16 carbons in the alkanoyl chain and 1 to 4 carbon atoms in the alkyl chain, and 2) an effective amount of one or more saturated C8-C14 fatty acid monoglycerides combined so that the minimum amount of the $N^\alpha$-alkanoyl-dibasic amino acid alkyl ester decreases synergistically with increasing concentration of the saturated C8-C14 fatty acid monoglycerides between the ratios of 9:1 to 1:9 wherein the total amount of antimicrobial, as a % by weight, is unchanged.

13. The method of claim 12 in which the concentration of antimicrobial composition applied is between 15 ppm and 20,000 ppm.

14. The method of claim 12 in which the concentration of antimicrobial composition applied is between 60 ppm and 10,000 ppm.

15. The method of claim 12 in which the $N^\alpha$-alkanoyl-dibasic amino acid alkyl ester salt is selected from the group consisting of an $N^\alpha$-lauroyl arginine ethyl ester salt and N$\alpha$-cocoyl arginine ethyl ester salt and the saturated C8-C14 fatty acid monoglyceride is glycerol monolaurate.

16. The method of claim 12 in which the anionic component of the $N^\alpha$-alkanoyl-dibasic amino acid alkyl ester salt is selected from hydrochloride, acetate and lactate.

17. A method of preservation of a food product by the application of 15ppm to 1 wt. % of a composition comprising 1) an $N^\alpha$-alkanoyl-L-arginine ethyl ester salt with a solubility of more than 50 ppm in water at RT and 2) an glycerol mono-laurate, combined so that the minimum amount of the $N^\alpha$-alkanoyl-dibasic amino acid alkyl ester decreases synergistically with increasing concentration of the saturated C8-C14 fatty acid monoglycerides between the ratios of 9:1 to 1:9 wherein the total amount of antimicrobial, as a % by weight, is unchanged.

18. A method of claim 17 in which the anion of the $N^\alpha$-alkanoyl-L-arginine ethyl ester salt is hydrochloride, acetate or lactate.

19. The method for preserving food products according to claim 17 wherein said food products are meat, poultry products, fish, crustaceans, vegetables, greens, emulsions, sauces, confectionery, candies, chewing gum, bakery, dairy products, egg-based products, jams, jellies, beverages, juices, wines and beers.

* * * * *